United States Patent
Kim et al.

(10) Patent No.: US 10,937,548 B2
(45) Date of Patent: Mar. 2, 2021

(54) COMPUTERIZED SYSTEM FOR EFFICIENT AUGMENTATION OF DATA SETS

(71) Applicant: Wisconsin Alumni Research Foundation, Madison, WI (US)

(72) Inventors: Won Hwa Kim, Madison, WI (US); Seong Jae Hwang, Madison, WI (US); Nagesh Adluru, Madison, WI (US); Sterling Johnson, Fitchburg, WI (US); Vikas Singh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 605 days.

(21) Appl. No.: 15/333,688

(22) Filed: Oct. 25, 2016

(65) Prior Publication Data
US 2018/0113990 A1    Apr. 26, 2018

(51) Int. Cl.
| | |
|---|---|
| *G16H 50/30* | (2018.01) |
| *G16H 10/20* | (2018.01) |
| *G16H 10/60* | (2018.01) |
| *G16H 15/00* | (2018.01) |

(52) U.S. Cl.
CPC ............. *G16H 50/30* (2018.01); *G16H 10/20* (2018.01); *G16H 10/60* (2018.01); *G16H 15/00* (2018.01)

(58) Field of Classification Search
CPC ........ G16H 50/30; G16H 15/00; G16H 10/60; G16H 10/20
See application file for complete search history.

(56) References Cited

U.S. PATENT DOCUMENTS

| | | | | |
|---|---|---|---|---|
| 2002/0103512 A1* | 8/2002 | Echauz | ................ | A61B 5/0482 607/9 |
| 2005/0228650 A1* | 10/2005 | Huang | ................ | H04R 25/606 704/205 |
| 2008/0154816 A1* | 6/2008 | Xiao | ........................ | G06N 3/02 706/15 |
| 2011/0093249 A1* | 4/2011 | Holmes | ................... | G06F 19/00 703/6 |
| 2011/0251985 A1* | 10/2011 | Waxman | .................. | A61B 5/08 706/20 |
| 2014/0279746 A1* | 9/2014 | De Bruin | ................. | A61B 5/00 706/12 |
| 2016/0140300 A1* | 5/2016 | Purdie | ................. | G06F 19/3481 705/2 |

(Continued)

OTHER PUBLICATIONS

Wang et al. "Similarity network fusion for aggregating data types on a genomic scale", Mar. 2014 Nature America, Inc. Nature methods, vol. 11 No. 3. (Year: 2014).*

(Continued)

*Primary Examiner* — Aleksandr Kerzhner
*Assistant Examiner* — Maher N Algibhah
(74) *Attorney, Agent, or Firm* — Boyle Fredrickson, S.C.

(57) ABSTRACT

A method of improving data sets, for example, of patients, each being characterized by relatively low-cost medical data, identifies those patients where the acquisition of higher cost medical data would best inform an estimate of the higher cost medical data for the remaining patients. In this way scarce medical resources can be more efficiently applied in characterizing a potential patient pool, for example, for a clinical trial when resources are not available for extensive medical characterization of each trial participant.

11 Claims, 2 Drawing Sheets

(56) References Cited

U.S. PATENT DOCUMENTS

2016/0154010 A1* 6/2016 O'Bryant ........... G01N 33/6896
506/9
2018/0113982 A1* 4/2018 Asthana ................ G06F 19/324

OTHER PUBLICATIONS

Troyanskaya et al. "Missing value estimation methods for DNA Microarrays", 2011 Oxford University Press, vol. 17 No. 6, pp. 520-525. (Year: 2011).*

* cited by examiner

COMPUTERIZED SYSTEM FOR EFFICIENT AUGMENTATION OF DATA SETS

STATEMENT REGARDING FEDERALLY SPONSORED RESEARCH OR DEVELOPMENT

This invention was made with government support under AG021155, AG040396 and AG033514 awarded by the National institutes of Health and IIS1252725 and CCF1320755 awarded by the National Science Foundation. The government has certain rights in the invention.

CROSS REFERENCE TO RELATED APPLICATION

N/A

BACKGROUND OF THE INVENTION

The present invention relates to a method of augmenting data sets, for example, data characterizing patients' clinical tests, by undertaking selective, additional data acquisition (for example, additional clinical measurements) to efficiently estimate missing data when not all data can be practically obtained.

In clinical studies of patients, it can be important to characterize potential patients for the study with respect to their likelihood of developing a given medical condition. For example, in a clinical study of Alzheimer treatments, it would be desirable to have a pool of test patients who are all likely to experience Alzheimer's disease. Having a "pre-screened" pool of patients can increase the statistical insight provided by the study, for example, in this case, because it can be assumed that patients who ultimately do not experience Alzheimer's disease were beneficially affected by the treatment being studied.

For Alzheimer's disease as well as other diseases, it can be difficult to determine in advance whether an individual is ultimately likely to have Alzheimer's disease in the future. This is a particular problem, when the treatment being studied must be initiated many years before Alzheimer's disease presents. Currently, Alzheimer's risk is studied by clinical measurements including, for example, PET studies, for example, using radio chemicals, such as $^{11}C$ Pittsburgh compound B. Such clinical measurements are costly in terms of dollar outlay, availability, procedure time, and patient inconvenience (collectively termed high-cost data). For this reason, such studies may rely heavily on non-imaging tests such as patient questionnaires or laboratory tests or relatively economical image/image-derived measurements that are less costly in terms of dollar outlay, availability, procedure time or patient inconvenience (collectively termed low-cost data). Generally, the high-cost procedures can greatly improve the accuracy of characterization of a patient who is likely to have Alzheimer's disease or not but are impractical for large studies.

SUMMARY OF THE INVENTION

The present inventors have recognized that predictive clinical measurements, both high-cost data, and to data, relate to a unifying underlying condition and that for this reason it should be possible to estimate the values of high-cost data for some individuals using measured low-cost and high-cost data for other similar individuals where the evaluation of similarity uses low-cost data. In this respect, the present invention provides a system for identifying those patients who can best serve as proxies for estimating the high-cost data of patients other than the proxies. This identification of proxies allows focused and selective, acquisition of additional high-cost data for some patients. Using this additional, high-cost data, the invention provides a method of better estimating high-cost data for the remaining patients.

Specifically, the invention, provides a computerized system for selectively augmenting a data set providing related objects each characterized by a first type of data, the computerized system including at least one electronic computer having a memory for holding a stored program. The stored program is executed to use the first type of data of the objects to generate a graph of the objects and then to use a wavelet expansion to identify proxy objects of the graph. Based on the identification of the proxy objects, the invention creates an augmented data set by collecting a second type of data, different from the first type of data, for the proxy objects. This augmented data set maximizes the value of the additional data collection.

It is thus a feature of at least one embodiment of the invention to provide a way of determining where scarce data collection resources should be allocated in order to improve the value of an entire data set. The wavelet transform on graphs provides a way of operating on a generalized graph (capturing similarity between objects) that is sensitive to the interrelatedness of the objects (in the transform domain) while localizing that interrelatedness to a particular object (in the graph domain) to identify objects where additional data would be most valuable.

The augmented data set may be used to produce an estimation of the second type of data for objects other than the proxy objects.

It is thus a feature of at least one embodiment of the invention to use the selected additional data collection to provide improved estimates of missing data for the remaining objects.

The estimation may employ minimization of an estimation error in a frequency domain of the graph subject to a band limited constraint and a subsequent inverse transformation from the frequency domain back into the graph.

It is thus a feature of at least one embodiment of the invention to incorporate a constraint of band limiting property into the estimation process by performing optimization in the frequency domain allowing reconstruction of estimated values through a simple inverse transformation.

The estimated type of data may be used to characterize the objects according to some predetermined criterion.

It is thus a feature of at least one embodiment of the invention to use additional data collected on particular objects to enhance the characterization of all objects with respect to a given criterion.

The objects may be patients for a clinical trial and the first type of data may represent a low-cost data for the patients and the second type of data may, represent higher cost data for the patients and the estimated type of data for the entire set of patients may be used to select patients for a clinical trial according to the predetermined criterion where the cost, of acquisition is minimized by not collecting the second type of data for every patient.

It is thus a feature of at least one embodiment of the invention to greatly, reduce the cost of important clinical trials particularly those that require substantial data collection on the individuals including significant high-cost data as a tool to identify the population appropriate for testing the drug or therapy under evaluation.

The first type of data and second type of data may be medical measurements related to Alzheimer risk and the clinical trial may relate to Alzheimer treatments applied before Alzheimer disease has been identified and the predetermined criterion may select patients likely to experience Alzheimer's disease.

It is thus a feature of at least one embodiment of the invention to provide improved patient pools for clinical studies for diseases like Alzheimer's disease that would otherwise require large numbers of prohibitively high-cost data collection.

The graph may be non-Euclidean and may have nodes representing each object and edges based on the similarity of data elements of the first data set of the objects. Non-Euclidean here means that the distances (or similarities) between pairs of nodes in the graph may not satisfy the classical Euclidean distance definition.

It is thus a feature of at least one embodiment of the invention to provide a technique that can be used with non-Euclidean graphs of the type likely to be generated by multiparameter clinical tests.

The step of creating the augmented data set may collect the second type of data only for selected of the proxy objects.

These particular features and advantages may apply to only some embodiments falling within the claims and thus do not define the scope of the invention.

DETAILED DESCRIPTION OF THE PREFERRED EMBODIMENT

Figure 1:
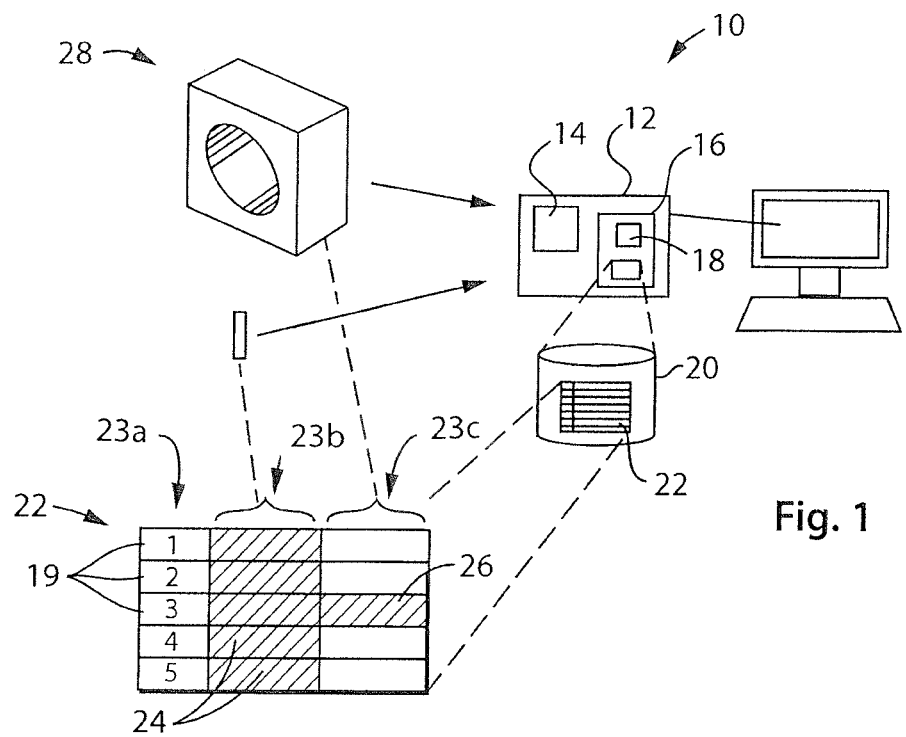
FIG. 1 is a data flow diagram of a system for collecting clinical data for patients including both high and low-cost data as stored in a table for processing by an electronic computer.

Referring now to FIG. 1, a system for data augmentation 10 may provide an electronic computer 12 having one or more processors 14 communicating with an electronic memory 16 holding a stored program 18 whose operation will be discussed below. Electronic memory 16 may, for example, include database memory 20 holding one or more data tables 22 containing patient data.

Logically the table 22 may provide for multiple rows associated with different patients 19 (here identified by the numbers 1-5 in a first column 23a). Multiple additional columns 23b of each row may hold low-cost data 24 associated with each patient 19, for example, obtained using low-cost techniques such as patient questionnaires or simple laboratory tests or the like. Generally, each patient 19 will have low-cost data 24.

Later additional columns 23c may hold some high-cost data 26, for example, obtained through an imaging machine 28 such as a PET scanner performing scans of radio chemicals such as, $^{11}C$ Pittsburgh compound B, for example, or a magnetic resonance imaging (MRI) scanner providing diffusion-weighted MRI images.

Figure 2:
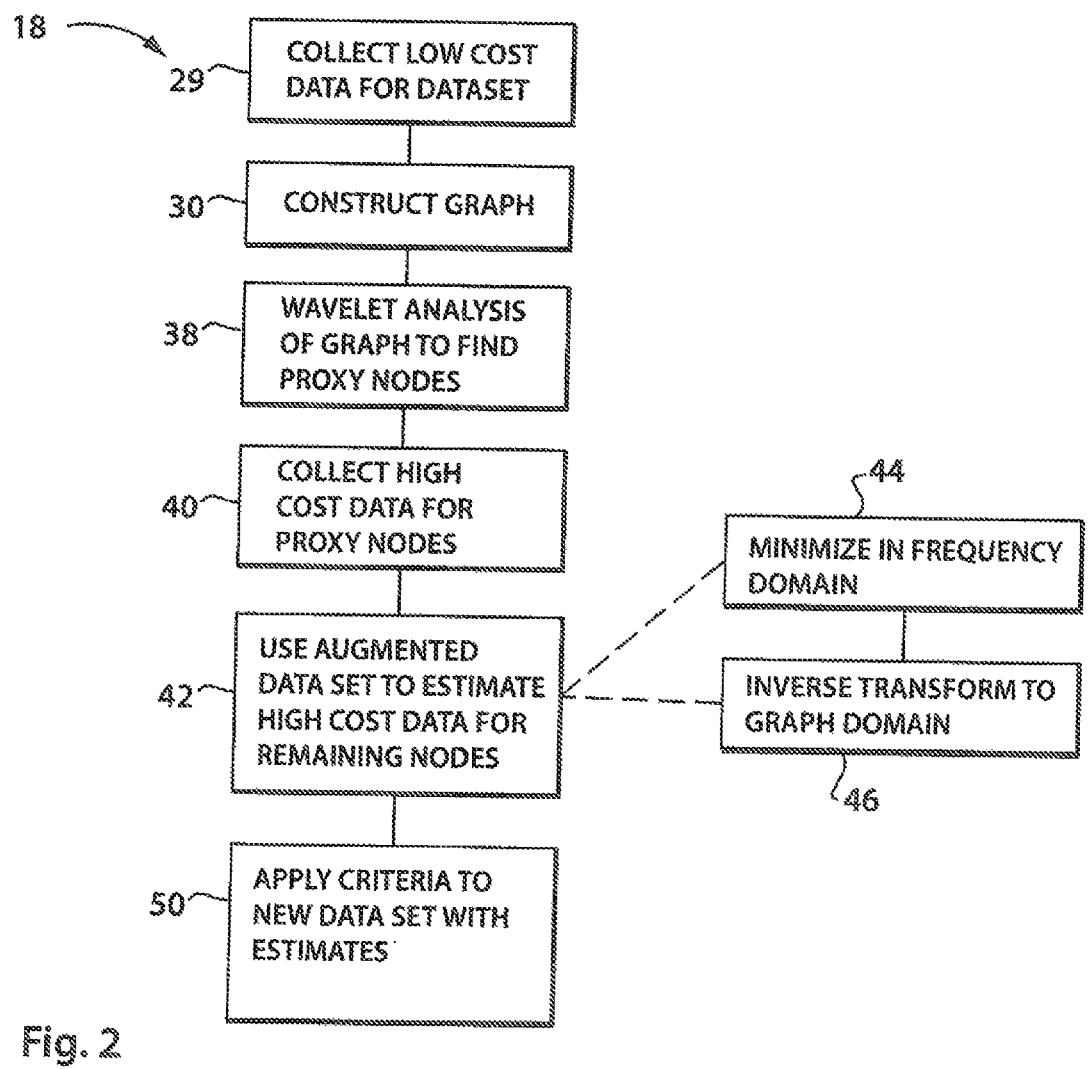
FIG. 2 is a flowchart of a program executed by the computer of FIG. 1 for identifying particular individuals or whom additional high-cost data should be collected and for using this additional high-cost data to estimate high-cost data for other patients ultimately to be used to qualify patients with respect to both high and low-cost data.

This collection of data to form data table 22 holding a data set is indicated by process block 29 of FIG. 2 and may be performed using standard computer entry and data storage techniques, for example, associated with database management.

Figure 3:
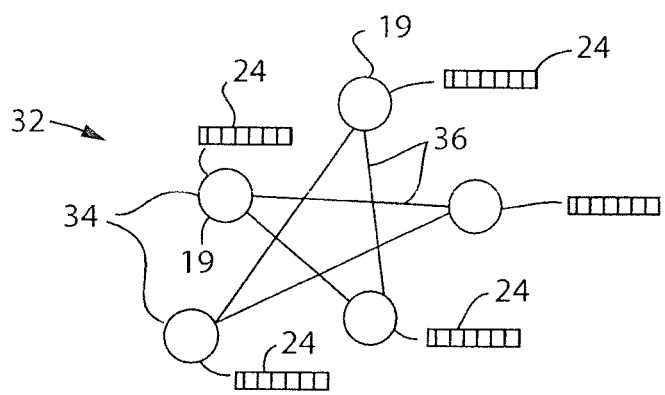
FIG. 3 is a simplified representation of the graph structure logically representing the data of the table of FIG. 1.

At succeeding process block 30 and referring also to FIG. 3, the data of table 22 may be used to construct a graph 32 logically providing multiple nodes 34 connected by edges 36. Each node 34 represents a different patient 19 and the data, for that patient 19 and the edges 36 have a length based on a similarity between the low-cost data 24 associated with the nodes 34 of the edge 36. For example, the length and edge 36 may be a multidimensional Euclidean distance between vectors representing the data 24. The resulting graph 32, however, will generally be a non-Euclidean, graph 32 meaning that a physical model with straight-line edges, between the nodes 34 in multiple dimensions is not necessarily possible given the length of the edges 36.

The constructed graph 32 may be stored in tables providing an adjacency matrix and degree matrix generally understood in the art and discussed further below.

Per process block 38 of FIG. 2, a wavelet analysis of the graph 32 is then conducted to identify nodes 34 that will serve as "proxy" nodes, being defined herein as nodes 34 where the collection of additional high-cost data 26 will maximize the ability to estimate high-cost data 26 for the other nodes 34 not having the high-cost data 26. Generally, the wavelet analysis will determine how much energy is preserved at a given node n for a specific scale s in frequency space over the range of the wavelet used for analysis. The more energy that a node 34 has, the more likely it is that the estimated high-cost data 26 for that node will be accurate on that specific node 34. Accordingly, the best proxy nodes will be nodes 34 having low energy value where additional high-cost data 26 is required for an accurate estimate.

Specifically, the wavelet analysis may be according to the following equation (1)

$$p_s(n) = \frac{1}{Z_s}\psi_n(s,n) = \frac{1}{Z_s}\sum_{l=0}^{N-1} h(s\lambda_l)\chi_l(n)^2 \qquad (1)$$

where
n is the node index;
$\psi_n(s,n)$ is the mother wavelet function having a scale s and translation values localized at each node index n;
h( ) is a filter for wavelets which can be, any known filter for wavelets such as Morlet, Meyer, Difference of Gaussians (DOG) etc.;
$\lambda_l$ and $\chi_l$ are pairs of eigenvalues and corresponding eigenvectors of a graph Laplacian L operator. The L operator is a matrix described by a difference between a matrix representing the graph 32 as an adjacency matrix A where each element $a_{i,j}$ of this adjacency matrix denotes the weight of an edge 36 between the ith and jth nodes 34 of the graph 32 and a degree matrix D being a diagonal matrix where the ith diagonal is the sum of the edge weights connected to the ith node. In this case L=D−A. L is a self-a joint and positive semi-definite operator and $Z_s$ is a normalizing factor $$Z_s = \sum_{n=1}^{N} \psi_n(s, n)$$

computed over the selected wavelet.

The formulation in (1) is especially useful when the distribution is known prior to the analysis by imposing higher weights on the frequency band where the signal is concentrated.

Figure 4:
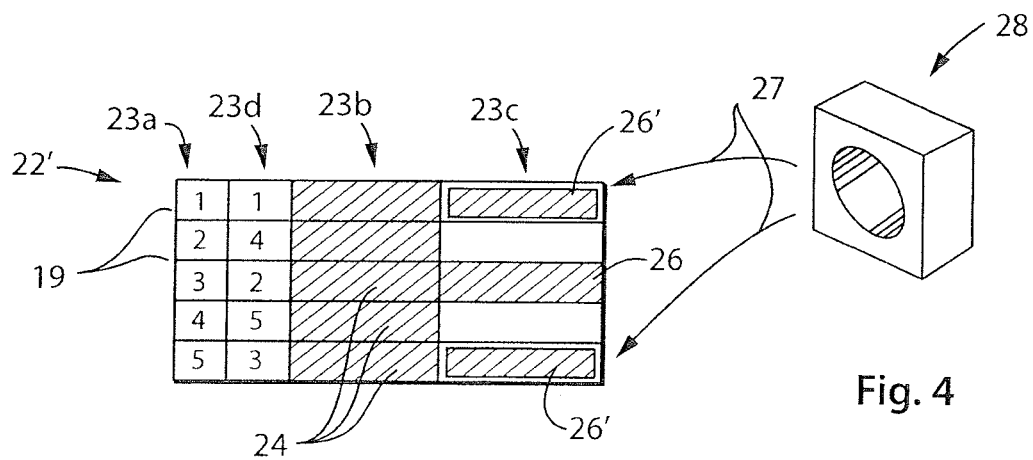
FIG. 4 is a data flow diagram of the acquisition of additional high-cost data to supplement the table of FIG. 1 based on an analysis of the graph of FIG. 3.

As shown in FIG. 4, the probability values may be used to establish a new column 23d in table 22' listing those nodes 34 (rows of table 22') that would be most benefited to have additional data collected.

Referring now to FIGS. 2 and 4, per process block 40, additional high-cost data 26' is then collected (indicated by arrows 27) for proxy nodes (in this, example being nodes 1 and 5) as guided by equation (1). For example, this additional high-cost data 26' may be collected using imaging machine 28 and the processes described above. This data is then entered into the table 22' for the selected nodes 34. Generally, at the conclusion of this process, high-cost data 26 or high-cost data 26' will not be needed for many of the rows of graph 32 as depicted. The result of this data, collection process will be termed augmented data table 22'.

The resulting augmented data set (where all additional high-cost data 26' that is budgeted has been acquired) may then be used to estimate, high-cost data 26 for those nodes 34 where it has not been collected per process block 42.

This estimation process may, for example, be implicit in a general use of the high-cost data in fitting the augmented data set to a multidimensional function using, for example, regression, machine learning, or linear program associated with a convex problem. These approaches have three weaknesses: (1) they do not take into account whether the reconstructed signal is bandlimited; (2) they provide a solution that is insensitive to whether the estimated data for the un-sampled nodes 34 is correct; and (3) an analytic solution is not easily obtainable without a regularizer Accordingly, the present invention provides a two-step estimation process including a minimization of an objective function after a frequency domain transformation of the graph 32 (the data of table 22'), as indicated by process block 44, followed by an inverse transformation of the minimized form of the graph back to the graph domain as indicated by process block 46.

More specifically, in process block 44, the minimization reduces the error in the sampled nodes according to the following equation (2)

$$\hat{g}_k^* = \arg\min_{\hat{g}_k \in \mathcal{R}^k} \left\| P_\Omega^{-\frac{1}{2}} (MV_k \hat{g}_k - y)) \right\|_2^2 + \gamma (V_k \hat{g}_k)^T h(L) V_k \hat{g}_k \quad (2)$$

where $\hat{g}_k$ are the first k coefficients of a function $\hat{g}_l$, $\Sigma_{n=1}^{N} g(n) \chi_i(n)$ being the Fourier transform of function g representing the augmented graph 32 (the data of table 22'); and $P_\Omega = \text{diag}(p(\Omega))$ where $\Omega$ is the index of high-cost data 26' $\{\omega_1, \ldots \omega_m\}$ of m nodes 34 yielding $y(i)=f(\omega_i)$ where $\forall_i \in \{1, 2, \ldots, m\}$.

M is a projection operator $M_{n \times N}$ based on the new high-cost data 26 and 26' as follows:

$$M_{i,j} = \begin{cases} 1 & \text{if } j = \omega_i \\ o & \text{otherwise} \end{cases};$$

$$h(L) = \sum_{l=0}^{N-1} h(\lambda_l) \chi_l \chi_l^T;$$

$V_k$ is a matrix with eigenvector column vectors $V_k = [\chi_0, \ldots, \chi_{k-1}]$; and $\gamma$ is an arbitrary convergence variable, for example, selected experimentally in one embodiment to have a value of 0.01.

Equation (2) is minimized as a convex problem by computing where the derivative becomes zero providing estimated frequency space values of node data that are band limited to k values (the highest value of k being much less than N, the number of nodes).

The optimum solution to $\hat{g}_k^*$ must satisfy the condition:

$$(V_k^T M^T P_\Omega^{-1} M V_k + \gamma V_k^T h(L) V_k) \hat{g}_k^* = V_k^T M^T P_\Omega^{-1} y \quad (3)$$

which reduces to:

$$(V_k^T M^T P_\Omega^{-1} M V_k + \gamma h(\Lambda_k)) \hat{g}_k^* = V_k^T M^T P_\Omega^{-1} y \quad (4)$$

where $\Lambda_k$ is a k×k diagonal matrix where the diagonals are the first k eigenvalues of L.

The values of $\hat{g}_k^*$ are then used to recover a low-ranked estimation of $g^* = V_k \hat{g}_k^*$ that reconstructs to f using the inverse Fourier transform to yields a graph 32. The nodes of this reconstructed graph 32 that previously did not have high-cost data 26 now have estimated high-cost data 26" reflecting estimates of the high-cost data elements for those rows (nodes 34).

Note that limiting the transformation process to k eigenvalues greatly reduces the complexity of the problem rendering the solution more efficient. Moreover the filtering operation of h( ) on L is much simpler.

Figure 5:
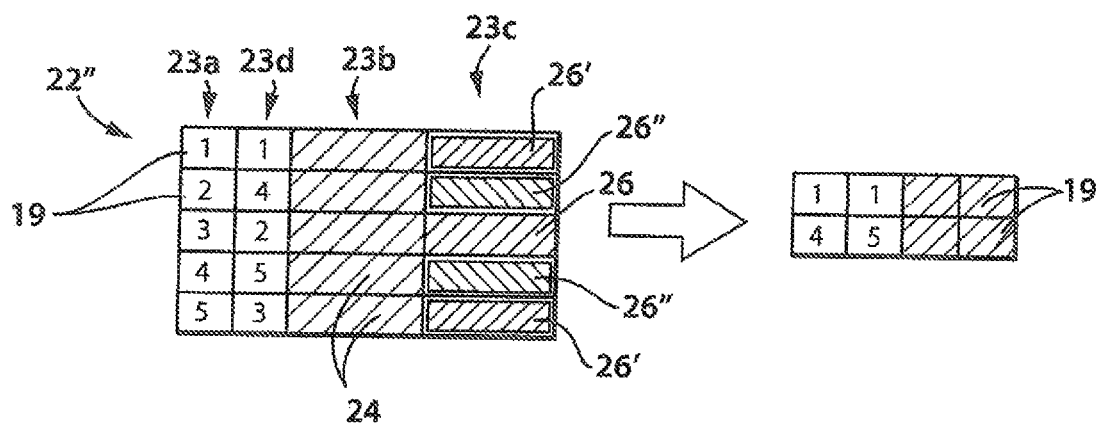
FIG. 5 is a diagram showing the reconstructed data as applied to a criterion, for example, for selecting a pool of patients for clinical trial.

Referring now to FIGS. 2 and 5, the table 22" then provides a complete set of low-cost data 24 and high-cost data 26, the latter formed of collected data and estimated data (collectively the estimated data set). This data may then be used for a variety of purposes. In one important example, the data may be applied to a selection, criterion per process block 50. This selection process, indicated by arrow 52, provides subset of particular rows and hence patients 19 based on a complete understanding of the data for each row (patient 19). It will be appreciated that, to the extent that the present invention identifies those individuals where more complete knowledge of the individuals improves the characterization of others not extensively characterized, the invention can also provide benefits, for example, to reduce the cost of diagnoses. By taking additional effort to identify and characterize certain individuals who are closely related to uncharacterized individuals, the predictive power of lower-cost screening can be better leveraged, for screening the population at large.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified, forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. A computerized system for selectively augmenting a data set of data describing objects of a group of related objects each object characterized by a first type of data, the computerized system comprising at least one electronic computer having a memory for holding a stored program and executing to:
   (a) use the first type of data of the objects to generate a graph of the objects providing multiple nodes each representing a different object;
   (b) use a wavelet expansion operating on the graph to identify a limited set of proxy objects from among the group and representative of the group with respect to a second type of data of the objects but being less than the number of objects in the group;
   (c) based on the identification of the proxy objects, create an augmented data set by collecting the second type of data different from the first type of data for the proxy objects and not for the objects other than the proxy objects; and
   (d) using the augmented data set of the proxy objects and information of the graph to produce estimated data estimating the second type of data for objects, represented in the group of the augmented data set, other than the proxy objects, where the second type of data has not been collected;
   wherein the wavelet expansion is in accordance with the equation:

$$p_s(n) = \frac{1}{Z_s} \psi_n(s, n) = \frac{1}{Z_s} \sum_{l=0}^{N-1} h(s\lambda_l) \chi_l(n)^2 \quad (1)$$

where:
n is a node index;
$\psi_n(s,n)$ is a mother wavelet function having a scale s and translation values localized at each node index n;
h( ) is a filter for wavelets;

$\lambda_l$ and $\chi_l$ are pairs of eigenvalues and corresponding eigenvectors of a graph Laplacian L operator; and
$Z_s$ is a normalizing factor $$Z_s = \sum_{n=1}^{N} \psi_n(s, n)$$

computed over a selected wavelet.

2. The computerized system of claim 1 wherein the estimation employs minimization of an estimation error in a frequency domain of the graph subject to a band limitation and a subsequent inverse transformation from the frequency domain back into the estimated data of the graph.

3. The computerized system of claim 1 wherein the estimated data is used to characterize the objects according to predetermined criterion.

4. The computerized system of claim 3 wherein the objects are patients for a clinical trial and the first type of data has a first cost and the second type of data has a second cost higher than the first cost and wherein the estimated data can be used for downstream analyses of the clinical study.

5. The computerized system of claim 4 wherein the first type of data and second type of data represent medical measurements related to Alzheimer risk and the clinical trial relates to analyses of the second type of data the analyses being at least one of categorical analyses and statistical analyses.

6. The computerized system of claim 1 wherein the graph is in non-Euclidean spaces and has nodes representing each object and edges based on a similarity of data elements of the first data set of the objects.

7. A method of selectively augmenting a data set providing related objects each characterized by a first type of data, the method operating on at least one electronic computer having a memory for holding a stored program and executing to perform the steps comprising:
   (a) using the first type of data of the objects to generate a graph of the objects;
   (b) using a wavelet expansion to identify proxy objects of the graph to identify a limited set of proxy objects from among the group and representative of the group with respect to a second type of data of the objects but being less than the number of objects in the group;
   (c) based on the identification of the proxy objects, creating an augmented data set by collecting the second type of data different from the first type of data for the proxy objects; and
   (d) using the augmented data set of the proxy objects and the graph to produce estimated data estimating the second type of data for objects of the group of the augmented data set other than the proxy objects where the second type of data has not been collected;
   wherein the wavelet expansion is in accordance with the equation:

$$p_s(n) = \frac{1}{Z_s} \psi_n(s, n) = \frac{1}{Z_s} \sum_{l=0}^{N-1} h(s\lambda_l) \chi_l(n)^2 \quad (1)$$

where:
n is a node index;
$\psi_n(s,n)$ is a mother wavelet function having a scale s and translation values localized at each node index n;

h( ) is a filter for wavelets;
$\lambda_l$ and $\chi_l$ are pairs of eigenvalues and corresponding eigenvectors of a graph Laplacian L operator, and
$Z_s$ is a normalizing factor $$Z_s = \sum_{n=1}^{N} \psi_n(s, n)$$

computed over a selected wavelet.

8. The method of claim 7 wherein the estimation employs minimization of an estimation error in a frequency domain of the graph subject to a band limitation and a subsequent inverse transformation from the frequency domain back into the graph.

9. The method of claim 7 wherein the objects are patients for a clinical trial and the first type of data has a first cost and the second type of data has a second cost higher than the first cost and wherein the estimated data can be used for downstream analyses of the clinical study.

10. The method of claim 7 wherein the first type of data and second type of data represent medical measurements related to Alzheimer's risk and the clinical trial relates to analyses of the second type of data, the analysis providing at least one of a categorical analyses and statistical analyses identifying the effects from Alzheimer's disease.

11. The method of claim 9 wherein the graph is in non-Euclidean spaces and has nodes representing each object and edges based on a similarity of data elements of the first data set of the objects.

* * * * *